United States Patent [19]

James B. Kimble et al.

[11] Patent Number: 5,105,045
[45] Date of Patent: Apr. 14, 1992

[54] METHOD OF OXIDATIVE CONVERSION

[75] Inventors: James B. Kimble, Bartlesville; John H. Kolts, Ochelata, both of Okla.

[73] Assignee: Phillips Petroleum Company, Bartlesville, Okla.

[21] Appl. No.: 597,913

[22] Filed: Oct. 15, 1990

Related U.S. Application Data

[62] Division of Ser. No. 742,335, Jun. 7, 1985, abandoned.

[51] Int. Cl.$^5$ .................................................. C07C 2/00
[52] U.S. Cl. .................................... 585/500; 585/654; 585/656; 585/658; 585/700; 585/400; 585/415; 585/417; 585/418; 585/943
[58] Field of Search ............... 585/500, 654, 656, 658, 585/700, 400, 415, 417, 418, 943

[56] References Cited

U.S. PATENT DOCUMENTS

| | | | |
|---|---|---|---|
| 3,308,198 | 10/1965 | Bajars | 260/680 |
| 4,368,346 | 1/1983 | Eastman | 585/658 |
| 4,513,164 | 4/1985 | Olah | 585/700 |
| 4,544,784 | 10/1985 | Sofranko et al. | 585/500 |
| 4,544,785 | 10/1985 | Withers et al. | 585/500 |

Primary Examiner—Patrick P. Garvin
Assistant Examiner—Patrick P. Irzinski
Attorney, Agent, or Firm—K. K. Brandes

[57] ABSTRACT

A method for the oxidative conversion of feed organic compounds, such as methane and ethane, to product organic compounds, such as ethylene, in the presence of a free oxygen containing gas and a contact material comprising: (1) Group IA and/or Group IIA metals/$O_2$/halogen; (2) Group IA metals/La Series metals/$O_2$/halogen and, optionally, Group IIA metals; (3) Group IA metals/Zn/$O_2$/halogen and, optionally, Group IIA metals; (4) Group IA metals/Ti or Zr/$O_2$/halogen and, optionally, Group IIA metals; (5) Group IA and/or IIA metals/phosphate/halogen or (6) Co/Zr, Zn, Nb, In, Pb and/or Bi/P/$O_2$halogen, and, optionally, Group IA metals and/or S, in which a contact material containing no halogen or an ineffective amount are activated and/or regenerated by contacting them with a halogen and, when the contact material is contact material (6), with a reducing agent or both a reducing agent and a halogen. A method of making the contact materials is also disclosed in which they are prepared without a halogen and calcined in air and the halogen is supplied by, thereafter, treating them with a halogen and, when the contact material is contact material (6), treating it with a reducing agent to reduce its state of oxidation, prior to use, preferably in the reaction zone in which it is to be used.

20 Claims, No Drawings

METHOD OF OXIDATIVE CONVERSION

This is a division of application Ser. No. 742,335, filed June 7, 1985 and now abandoned.

The present invention relates to a method for the oxidative conversion of feed organic materials to product organic materials, in the presence of a free oxygen containing gas, and reaction-promoting, solid contact materials. In another aspect the present invention relates to a method of preparing such solid contact materials and maintaining the activity thereof.

BACKGROUND OF THE INVENTION

Numerous processes are in use and have been proposed for the conversion of organic compounds and feedstocks to more valuable organic compounds and more valuable feedstocks, for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have, at one time or another, suggested that the function of the contact material involves a purely physical phenomenon, an adsorption-desorption process, either of atomic or molecular oxygen, either on the surface or occluded within the solid material, oxidation-reduction utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen-containing contact material, and, thereafter, reactivating or regenerating the contact material by again passing an oxidizing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks.

Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to promote pyrolytic reactions have been made. While some of these processes do, in fact, reduce the severity of the conditions, the conversion of the feedstock and the selectivity to ethylene are still quite low. Of particular interest in this phase of the art, are the oxidative dehydrogenation of alkanes, particularly alkanes having from 2 to 7 carbon atoms, and, still more particularly ethane, and the oxidative conversion of methane to ethylene. However, many of the processes for oxidative dehydrogenation and oxidative conversion of methane, which have been proposed, are subject to some or all of the previously mentioned deficiencies.

SUMMARY OF THE INVENTION

It is therefore an object of the present invention to provide an improved composition of matter and method of utilizing the same which overcomes the above and other disadvantages of the prior art. Still another object of the present invention is to provide an improved method of making, activating and/or reactivating contact materials for the oxidative conversion of organic compounds to other organic compounds, in the presence of a free oxygen containing gas. Another and further object of the present invention is to provide an improved method for the oxidative conversion of organic compounds to other organic compounds, in the presence of a free oxygen containing gas. Another and further object of the present invention is to provide an improved method for the oxidative conversion of alkane hydrocarbons to olefinic hydrocarbons, in the presence of a free oxygen containing gas. Still another object of the present invention is to provide an improved method for converting methane to higher hydrocarbons, in the presence of a free oxygen containing gas. A further object of the present invention is to provide a method for the oxidative conversion of organic compounds to other organic compounds resulting in improved conversion of feedstock. Yet another object of the present invention is to provide a method for the oxidative conversion of organic compounds to other organic compounds, resulting in improved selectivity to desired products. A further object of the present invention is to provide a method for the oxidative conversion of organic compounds to other organic compounds, resulting in improved conversion of feedstock and improved selectivity to desired products. Another and further object of the present invention is to provide a method for the oxidative conversion of organic compounds to other organic compounds, which utilizes temperatures below those of known processes. A still further object of the present invention is to provide a method for the oxidative conversion of organic compounds to other organic compounds, which reduces the energy requirements thereof. Another object of the present invention is to provide a method for the oxidative conversion of organic compounds to other organic compounds, which can be carried out in a continuous manner. Yet another object of the present invention is to provide a method for the oxidative conversion of organic compounds to other organic compounds, which extends the useful life of the contact material utilized. These and other objects of the present invention will be apparent from the following detailed description.

The present invention provides an improved method for the oxidative conversion of feed organic materials to product organic materials, comprising:

(a) contacting said feed organic materials and a free oxygen containing gas with a reaction-promoting, solid contact material containing at least one metal, oxygen and at least one halogen, under oxidative conversion conditions sufficient to convert said feed organic compounds to said product organic compounds; and (b) at least intervally contacting said solid contact material with at least one of a material containing at least one halogen and a material containing at least one reducing agent.

In a preferred embodiment the solid contact material is a solid contact material selected from the group consisting of:

(1) a solid contact material comprising: (A) at least one metal selected from the group consisting of Group IA metals, Group IIA metals and mixtures thereof, (B) oxygen and, (C) at least one material selected from the group consisting of halogen ions and compounds containing halogen ions; (2) a solid contact material comprising: (A) at least one metal selected from the group consisting of Group IA metals, (B) at least one metal selected from the group consisting of lanthanum Series metals, (C) oxygen, (D) at least one material selected from the group consisting of halogen ions and compounds containing halogen ions, and, optionally, (E) at least one Group IIA metal;

(3) a solid contact material comprising: (A) at least one metal selected from the group consisting of Group IA metals, (B) zinc, (C) oxygen, (D) at least one material selected from the group consisting of halogen ions and compounds containing halogen ions and, optionally, (E) at least one Group IIA metal;

(4) a solid contact material comprising: (A) at least one metal selected from the group consisting of Group IA metals, (B) at least one metal selected from the group consisting of titanium and zirconium, (C) oxygen, (D) at least one material selected from the group consisting of halogen ions and compounds containing halogen ions and, optionally, (E) at least one Group IIA metal;

(5) a solid contact material comprising: (A) at least one metal selected from the group consisting of Group IA metals, Group IIA metals, and mixtures thereof, (B) at least one material selected from the group consisting of phosphate radicals and compounds containing phosphate radicals and (C) at least one material selected from the group consisting of halogen ions and materials containing halogen ions; and (6) a solid contact material comprising: (A) cobalt, (B) at least one metal selected from the group consisting of zirconium, zinc, niobium, indium, lead and bismuth, (C) phosphorous, (D) oxygen, (E) at least one material selected from the group consisting of halogen ions and compounds containing halogen ions and, optionally, (F) at least one material selected from the group consisting of Group IA metals, sulfur, compounds containing sulfur and mixtures thereof;

and the solid contact material is at least intervally contacted with a material containing at least one halogen, when the contact material is selected from the group consisting of contact materials (1), (2), (3), (4) and (5), and with at least one of a material containing at least one halogen and a material containing at least one reducing agent, when the contact material is contact material (6).

In another aspect, the present invention relates to improved methods of making such contact materials when their reaction-promoting effect has degenerated.

DESCRIPTION OF THE PREFERRED EMBODIMENTS

The improved method of the present invention comprises: a method for the oxidative conversion of feed organic materials to product organic materials, comprising:

(a) contacting said feed organic materials and a free oxygen containing gas with a reaction-promoting solid contact material containing at least one metal, oxygen and at least one halogen under oxidative conversion conditions sufficient to convert said feed organic compounds to said product organic compounds; and (b) at least intervally contacting said solid contact material with at least one of a material containing at least one halogen and a material containing at least one reducing agent.

The nature of the present invention, the manner of practicing the invention and the best mode will be best understood by reference to the preferred solid contact materials which are selected from the group consisting of:

(1) a solid contact material comprising: (A) at least one metal selected from the group consisting of Group IA metals, Group IIA metals and mixtures thereof, (B) oxygen, and (C) at least one material selected from the group consisting of halogen ions and compounds containing halogen ions;

(2) a solid contact material comprising: (A) at least one metal selected from the group consisting of Group IA metals, (B) at least one metal selected from the group consisting of lanthanum Series metals, (C) oxygen, (D) at least one material selected from the group consisting of halogen ions and compounds containing halogen ions and, optionally, (E) at least one Group IIA metal;

(3) a solid contact material comprising: (A) at least one metal selected from the group consisting of Group IA metals, (B) zinc, (C) oxygen, (D) at least one material selected from the group consisting of halogen ions and compounds containing halogen ions and, optionally, (E) at least one Group IIA metal;

(4) a solid contact material comprising: (A) at least one metal selected from the group consisting of Group IA metals, (B) at least one metal selected from the group consisting of titanium and zirconium, (C) oxygen, (D) at least one material selected from the group consisting of halogen ions and compounds containing halogen ions and, optionally, (E) at least one Group IIA metal;

(5) a solid contact material comprising: (A) at least one metal selected from the group consisting of group IA metals, Group IIA metals, and mixtures thereof, (B) at least one material selected from the group consisting of phosphate radicals and compounds containing phosphate radicals and (C) at least one material selected from the group consisting of halogen ions and materials containing halogen ions; and (6) a solid contact material comprising: (A) cobalt, (B) at least one metal selected from the group consisting of zirconium, zinc, niobium, indium, lead and bismuth, (C) phosphorous, (D) oxygen, (E) at least one material selected from the group consisting of halogen ions and compounds containing halogen ions, and, optionally, (F) at least one material selected from the group consisting of Group IA metals, sulfur, compounds containing sulfur and mixtures thereof.

The solid contact material is contacted with a material containing at least one halogen, when the contact material is selected from the group consisting of contact materials (1), (2), (3), (4) and (5), and with at least one of a material containing at least one halogen and a material containing at least one reducing agent, when the contact material is contact material (6).

Processes for the oxidative conversion of feed organic materials to product organic materials, in accordance with the present invention, include the oxidative dehydrogenation of hydrocarbons, particularly alkanes having 2 to 7 carbon atoms, to other hydrocarbons, particularly ethylene, the oxidative conversion of methane to higher hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The solid contact materials of the present invention are particularly useful for the oxidative dehydrogenation of alkane hydrocarbons, having from 2 to 7 carbon atoms, to ethylene, and the oxidation conversion of methane to ethylene, in the presence of a free oxygen containing gas.

Preferred Group IA metals utilized in the contact materials are selected from the group consisting of lithium, sodium and potassium.

Preferred Group IIA metals are selected from the group consisting of magnesium, calcium, strontium, and barium.

Lanthanum series metals are preferably selected from the group consisting of lanthanum and cerium and, of the two, lanthanum is preferred.

Contact material (6) preferably includes zirconium. When a Group IA metal is utilized in this contact material, it is preferably selected from the group consisting of lithium, sodium and potassium, preferably sodium and still more preferably both sodium and potassium.

The halogen component is preferably chlorine.

The exact compositions and nature of the contact materials is not known and, accordingly, it is to be understood that the present invention is not to be limited to any particular theory concerning the composition or character of the contact materials. However, it is believed that the contact materials have the following observed characteristics.

Contact material (1) is believed to be in the form of oxides, carbonates, mixtures of oxides, mixtures of carbonates or mixtures of oxides and carbonates. Specifically, when Group IA or Group IIA metals alone are utilized these materials are believed to be predominately in either oxide or carbonate form. It is further believed that the oxide form is converted to the carbonate form during the conduct of the oxidative conversion in the presence of the free oxygen-containing gas. When both Group IA and IIA metals are present in this contact material, it is believed that the Group IA and Group IIA metals are in the form of oxides, carbonates, mixtures of oxides, mixtures of carbonates or mixtures of oxides and carbonates. As in the single metal contact materials, it is believed that the oxide forms are converted to carbonates during the course of the reaction. Also in the combination of Group IA and Group IIA metals, it is believed that the Group IIA metal is in its oxide form irrespective of the form of the Group IA metal.

The Group IA metals of contact material (2) are believed to be predominately in the form of oxides, carbonates, mixed oxides, mixed carbonates or mixtures of oxides and carbonates. The lanthanum series metals, particularly lanthanum and cerium, of this contact material are also believed to be in the form of oxides, carbonates, mixtures of oxides or mixtures of oxides and carbonates and when Group IIA metals are present they are likewise believed to be in these forms.

Similarly, the metals of contact material (3) are believed to be predominately oxides, carbonates or mixtures as indicated above.

In contact material (4), the Group IA metals are believed to be predominately in the oxide, carbonate or mixture form as set forth above. The titanium or zirconium of this contact material may also be predominately in the oxide or carbonate form, as specified above, as are Group IIA metals when present. However, it is believed more likely that the titanium and zirconium are predominately in the form of Group IIA metal titanates or zirconates, when Group IIA metals are utilized, and possibly some Group IA metal titanates or zirconates. The possibility also exists that Group IA metals alone may be in the form of titanates or zirconates or at least partially in this form.

Contact material (5) is believed to be in the form of Group IA metal phosphates, Group IIA metal phosphates or Group IA metal oxides and/or carbonates with Group IIA metal phosphates.

Contact material (6) is believed to be a complex mixture of oxides but may also contain some materials in carbonate form, phosphate radicals and, when utilized, sulfate radicals. As will be pointed out hereinafter, even though contact material (6) is believed to be a complex mixture of oxides, it is most effective in a reduced state of oxidation. Consequently it is either prepared in a reduced state of oxidation, preliminarily reduced in the reaction zone and/or maintained in a reduced state of oxidation during the reaction.

The presence of a halogen in each of the contact materials has been found to greatly increase the conversion of feed organic compounds to product organic compound, particularly the conversion of more saturated organic compounds to less saturated organic compounds and still more particularly the conversion of alkane hydrocarbons to olefinic hydrocarbons. However, the form in which the halogen is present in the contact material and a manner in which it functions are also unknown. Whatever the form of the halogen in the contact material, it is believed that it is present near or on the surface of the particles of contact material.

The contents and relative proportions of the various components of the contact materials does not appear to be highly critical. Accordingly, the components may be present in amounts anywhere from an effective amount to near 100 percent. When the term "effective amount" is utilized, with reference to the content of the components of the contact materials herein, this term is meant to include more than an insignificant amount and, thus, a small amount sufficient to effect the function of the contact material for the purpose for which it is utilized. However, preferred contact materials do contain certain compounds in major proportions and others in minor proportions. Where Group IA and/or Group IIA metals are utilized in contact materials (1), (2), (3), (4) or (5) and they are not in the form of electrically balanced compounds with the base or major component, such Group IA and Group IIA metals are preferably utilized in minor amounts, usually between about 0.1 and 50 weight percent, still more preferably between about 0.5 and 15 weight percent and optimally between about 1 weight percent and about 5 weight percent, expressed in terms of the elemental metal based on the total weight of the contact material. Halogens are also preferably utilized in minor amounts, usually between about 0.1 weight percent and 5 weight percent, expressed as elemental halogen based on the total weight of the contact material. In contact material (6) the cobalt and the metal selected from the group consisting of zirconium, zinc, niobium, indium, lead and bismuth are utilized as major components while the remaining components are utilized in minor amounts. By way of example, the preferable atomic ratio of cobalt to the metals selected from the group consisting of zirconium, zinc, niobium, indium, lead and bismuth is in the range of about 1/1 to about 20/1 and more preferably in the range of about 3/1 to 6/1. The phosphorous is preferably present in an amount of about 1 weight percent to about 10 weight percent and more preferably between about 2 weight percent and about 5 weight percent, expressed in terms of phosphorous oxide based on total weight of the contact material. Preferably, the alkali metal is present in concentrations of about 1 weight percent to about 10 weight percent and more preferably between about 2 weight percent and about 5 weight percent, also expressed in terms of alkali metal oxide based on the total weight of the contact material. Preferred concentrations of sulfur are in the range of about 1 weight percent to about 10 weight percent and more preferably between about 2 weight percent and about 5 weight percent, expressed in terms of elemental sulfur based on the total weight of the contact material. The halogen is preferably present in an amount between about 1 weight percent and about 10 weight percent and more preferably between about 2 weight percent and about 5 weight percent, expressed in terms of elemental halogen based on the total weight of the contact material.

The above-mentioned components can be mixed with or deposited on an "inert support material" adapted to harden or support the active materials. The term "inert support material", when utilized in this context, is meant to include any material which does not react with or exchange ions with the active components, has no significant functional effect on the production of desired or undesired products in the process for which the solid contact material is utilized and functions only as a hardening agent or support for the active components. Where such solid support material is utilized the weight of such solid support material is not included in the relative weights of the active components set forth above.

The components of the contact material can be derived from any suitable source of such materials, such as carbonates, oxides, hydroxides, nitrates, octoates, chlorides, phosphates, sulfides and sulfonates, of an organic or inorganic nature. The contact materials can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. When slurries, precipitates or the like are prepared, they will generally be dried, usually at a temperature sufficient to volatilize the water or other carrier, such as about 220° F. to about 450° F. In all cases, irrespective of how the components are combined and irrespective of the source of the components, the dried composition is calcined in the presence of a free oxygen containing gas, usually at temperatures between about 600° F. and about 1200° F. for from 1 to about 24 hours. As pointed out hereinafter, contact material (6) can be calcined in a reducing or inert atmosphereor an oxygen containing atmosphere.

The manner in which the contact materials of the present invention perform the reaction-promoting function is not fully understood. Accordingly, the present invention is not to be limited to any particular theory. However, several significant observations have been made in parallel work and in accordance with the present invention.

First, each of the components of contact materials (1), (2), (3), (4), (5) and (6), unless designated as optional, appear necessary and participate in the reaction promoting function thereof. Hence, simply because a particular component is present in an minor amount it cannot be categorized as a "promoter" or "active" component and the components present in major proportions cannot be categorized as inert "bases", "carriers" or "supports".

Secondly, with the exception of contact material (6), most of the contact materials do not promote oxidative conversion reactions or result in insignicant conversion of feed organic materials and/or insignificant selectivity to product organic compounds in the absence of a free oxygen containing gas. However, even in the case of contact material (6), frequent cycling of feed organic compounds, for production of product organic compounds, and a free oxygen containing gas, for reactivation or regeneration, is necessary, usually with purging with an inert gas between the conversion and activation steps, when oxygen is not fed continuously. In many cases the reaction step is several minutes long and the reactivation step is several minutes long and often the time required for reactivation is longer than the actual reaction time.

Third, in the use of contact materials (1) through (5), in a presence of a free oxygen containing gas, some contact materials appear to consume substantial amounts of oxygen while others consume insignificant amounts. Additionally, most of the oxygen consuming contact materials are single valent materials and thus have one state of oxidation.

Finally, it has been observed, in accordance with the present invention, that contact material (6) results in very poor conversion and/or selectivity, if it is in a high state of oxidation, and reduction of the state of oxidation is highly desirable.

Based on these observations it can be concluded that, irrespective of whether multivalent components are present in the contact materials, the reaction mechanism of the present invention is not oxidation-reduction. Accordingly, at least when the reactions are carried out in the presence of a free oxygen containing gas, in accordance with the present invention, it is not necessary that the contact material include multivalent components capable of undergoing oxidation-reduction or redox reactions, as taught by many workers in prior art.

It has also been found, in accordance with the present invention, that the halogen of the contact materials becomes depleted during the course of oxidative conversion in the presence of a free oxygen containing gas. Accordingly, when carrying out the oxidative conversion reaction, in accordance with the present invention, a material containing at least one halogen, such as gaseous halogen, for example, chlorine, methylchloride, methylenechloride and like compounds of the other halogens, is at least intervally contacted with the contact material. The material containing the halogen is preferably a normally gaseous material or will be in a vapor state under the operating conditions of the oxidative conversion reaction. In any event, in accordance with the present invention, the reaction-promoting activity of the contact material can be maintained throughout the conduct of the method by continuously adding the material containing the halogen to the organic feed compounds and free oxygen containing gas or by adding the material containing the halogen at intervals during the conduct of the method. In the latter case, the flow of feed organic compounds and free oxygen containing gas can be discontinued during the addition of the material containing the halogen, although this is not necessary.

The state of oxidation of solid contact materials (1), (2), (3), (4) and (5) does not appear to be critical and, normally, it is not necessary to contact any of these contact materials with a reducing agent in order to maintain their reaction-promoting activity. However, when these contact materials have been utilized in long production runs, occasional contacting of the contact material with a reducing agent may be beneficial. On the other hand, as indicated previously, the reaction-promoting effect of solid contact material (6) does appear to be affected by the degree of oxidation thereof. It has been found that after a period of use, in the presence of a free oxygen containing gas, there is a tendency for this contact material to become "overoxidized" and lose its reaction-promoting activity. However, in accordance with the present invention, it has been found that the reaction-promoting activity of this contact material can be maintained at near its peak activity by intervally contacting the solid contact material with a material containing at least one reducing agent. In practicing this aspect of the present invention, it is desirable to stop the flow of free oxygen containing gas during the contacting with the reducing agent. Any suitable reducing agent, preferably in a gaseous or vapor form, can be utilized, such as by hydrogen, lower alkanes, including, methane and ethane, etc. Conveniently, when the feed material contains methane, ethane or like reducing agents, the contact material can be treated by simply stopping the flow of free oxygen containing gas while maintaining the flow of feed containing the reducing agent. Further, in accordance with the present invention and as shown in the hereinafter presented examples, treatment with a combination of halogen and a reducing agent is superior to either alone. Such combination treatment can be carried out sequentially, in either sequence, or simultaneously. However, it has also been found that best results are obtained by first treating the contact material with a halogen and thereafter with a reducing agent. Where such combination treatment is practiced, the feed organic material and the free oxygen containing gas may be stopped during the treatment, the feed and oxygen can be continued during halogen treatment and the oxygen stopped only during treatment with the reducing agent, the oxygen only can be stopped during treatment with halogen and reducing agent or other variations which will occur to one skilled in the art. In any of these procedures, when the feed organic material is a reducing agent or contains a reducing agent, the flow of feed organic material would be continued or resumed for the reducing treatment.

Another embodiment of the present invention, based on these discoveries, comprises the following method for reactivating the solid contact material when its reaction-promoting activity has deteriorated.

In a method for the oxidative conversion of feed organic compounds to product organic compounds, in which said feed organic compounds and a free oxygen containing gas are contacted with a reaction-promoting, solid contact material containing at least one metal, oxygen and at least one halogen, under oxidative conversion conditions sufficient to convert said feed organic compounds to said product organic compounds, the improved method of reactivating said solid contact material, when its reaction-promoting effect has deteriorated, comprising:

at least intervally contacting said solid contact material with at least one of a material containing at least one halogen and a material containing at least one halogen and a material containing at least one reducing agent.

As in the oxidative conversion method, the preferred solid contact materials are selected from the group consisting of:

(1) a solid contact material comprising: (A) at least one metal selected from the group consisting of Group IA metals, Group IIA metals and mixtures thereof; (B) oxygen and (C) at least one material selected from the group consisting of halogen ions and compounds containing halogen ions;

(2) a solid contact material comprising: (A) at least one metal selected from the group consisting of Group IA metals, (B) at least one metal selected from the group consisting of lanthanum Series metals, (C) oxygen, (D) at least one material selected from the group consisting of halogen ions and compounds containing halogen ions and, optionally, (E) at least one metal selected from the group consisting of Group IIA metals;

(3) a solid contact material comprising: (A) at least one metal selected from the group consisting of Group IA metals, (B) zinc, (C) oxygen, (D) at least one material selected from the group consisting of halogen ions and compounds containing halogen ions, and, optionally, (E) at least one metal selected from the group consisting of Group IIA metals;

(4) a solid contact material comprising: (A) at least one metal selected from the group consisting of Group IA metals, (B) at least one metal selected from the group consisting of titanium and zirconium, (C) oxygen, (D) at least one material selected from the group consisting of halogen ions and compounds containing halogen ions and, optionally, (E) at least one metal selected from the group consisting of Group IIA metals;

(5) a solid contact material comprising: (A) at least one metal selected from the group consisting of Group IA metals, Group IIA metals and mixtures thereof, (B) at least one material selected from the group consisting of phosphate radicals and compounds containing phosphate radicals and (C) at least one material selected from the group consisting of halogen ions and compounds containing halogen ions; and (6) a solid contact material comprising: (A) cobalt, (B) at least one metal selected from the group consisting of zirconium, zinc, niobium, indium, lead and bismuth, (C) phosphorous, (D) oxygen, (E) at least one material selected from the group consisting of halogen ions and compounds containing halogen ions and, optionally, (F) at least one material selected from the group consisting of Group IA metals, sulfur, compounds containing sulfur and mixtures thereof.

The specific reactivation procedures, in accordance with this embodiment of the invention, are the same as those previously discussed in connection with the maintenance of the activity of the contact material in the method for oxidative conversion.

It has also been discovered that the solid contact materials of the present invention can be prepared without or with only small amounts of the halogen component and such component can be added by, thereafter, treating the calcined contact material with a material containing at least one halogen, preferably in a gaseous or vapor state. Such treatment can be preformed prior to disposing the contact material in the reaction zone in which the oxidative conversion reaction is to be carried out, but, preferably the calcined contact material is disposed in the reaction zone and treated with the halogen prior to the introduction of the organic feed material and free oxygen containing gas or along with the first portion of the organic feed and oxygen. This technique also results in more active contact materials, since it has also been found that, in at least some cases, it is difficult to incorporate an effective amount of halogen in the contact material during preparation and/or retain an effective amount of halogen in the contact material during preparation, particularly during calcining.

Contact material (6), as previously indicated, has another peculiarity, namely, that it produces substantially superior results if it is in a lower state of oxidation. Normally, in the preparation of this contact material, the combined components are dried in the presence of a free oxygen containing gas, usually air. As a result of the presence of the air at an elevated temperature, it is believed that at least some of the components of the contact material are in a high state of oxidation after drying and, therefore, are inefficient contact materials for the oxidative conversion reaction. Consequently, it has been the past practice to calcine the dried contact material in an inert or reducing atmosphere in order to reduce the oxidation level of the material. This, of course, is difficult and adds the expense of preparation. In accordance with the present invention, it has been found that the combined air-dried components of the contact material may be calcined in a conventional manner in the presence of a free oxygen containing gas, usually air, and, thereafter, pretreated, to reduce the level of oxidation, by contacting the calcined contact material with a material including at least one reducing material. Suitable reducing materials include hydrogen, lower alkanes such as methane, ethane, etc. This technique is even more convenient, to the extent that the preferred technique involves disposing a calcined contact material in the reactor in which the oxidative conversion reaction is to be carried out for the pretreatment with the reducing agent and, when methane or ethane are starting materials for the oxidative conversion reaction, such materials are already conveniently available. Contact material (6) can also be prepared without halogen, or with only a small amount of halogen, and the halogen also added during the pretreatment. Consequently, the pretreatment comprises contacting the air calcined contact material with both a material containing at least one halogen and a material containing a reducing agent. Such contacting may be simultaneous or in either sequence.

Therefore, another embodiment of the present invention comprises the following method of making a solid contact material as specified below.

A method of preparing a solid contact material containing at least one metal, oxygen and at least one halogen, adapted to promote the oxidative conversion of feed organic compounds to product organic compounds in the presence of a free oxygen containing gas and under oxidative conversion conditions, comprising:

(a) calcining compounds of said at least one metal in the presence of a free oxygen containing gas; and (b) thereafter, contacting the thus calcined compounds with at least one of a material containing at least one halogen and a material containing at least one reducing agent.

In the preferred embodiment, the contact material containing the metal, oxygen and the halogen, is a contact material selected from the group consisting of:

(1) a solid contact material comprising: (A) at least one metal selected from the group consisting of Group IA metals, Group IIA metals and mixtures thereof, (B) oxygen and (C) at least one material selected from the group consisting of halogen ions and compounds containing halogen ions;

(2) a solid contact material comprising: (A) at least one metal selected from the group consisting of Group IA metals, (B) at least one metal selected from the group consisting of lanthanum Series metals, (C) oxygen, (D) at least one material selected from the group consisting of halogen ions and compounds containing halogen ions and, optionally, (E) at least one metal selected from the group consisting of Group IIA metals;

(3) a solid contact material comprising: (A) at least one metal selected from the group consisting of Group IA metals, (B) zinc, (C) oxygen, (D) at least one material selected from the group consisting of halogen ions and compounds containing halogen ions, and, optionally, (E) at least one metal selected from the group consisting of Group IIA metals;

(4) a solid contact material comprising: (A) at least one metal selected from the group consisting of Group IA metals, (B) at least one metal selected from the group consisting of titanium and zirconium, (C) oxygen, (D) at least one material selected from the group consisting of halogen ions and compounds containing halogen ions and, optionally, (E) at least one metal selected from the group consisting of Group IIA metals;

(5) a solid contact material comprising: (A) at least one metal selected from the group consisting of Group IA metals, Group IIA metals and mixtures thereof, (B) at least one material selected from the group consisting of phosphate radicals and compounds containing phosphate radicals and (C) at least one material selected from the group consisting of halogen ions and compounds containing halogen ions; and (6) a solid contact material comprising: (A) cobalt, (B) at least one metal selected from the group consisting of zirconium, zinc, niobium, indium, lead and bismuth, (C) phosphorous, (D) oxygen, (E) at least one material selected from the group consisting of halogen ions and compounds containing halogen ions and, optionally, (F) at least one material selected from the group consisting of Group IA metals, sulfur, compounds containing sulfur and mixtures thereof.

The present invention and the advantages thereof are first illustrated by use in the oxidative dehydrogenation of ethane to ethylene in the presence of contact material (6).

The oxidative dehydrogenation of alkanes to other hydrocarbons, particularly ethane to ethylene, can be carried out under a wide range of conditions. Since conditions which favor high conversion of feedstock generally result in lower selectivities to the desired products, and vice versa, the conversion and selectivity can be balanced, as desired, to some extent, by selecting the composition of the contact material, and/or varying the conditions of operation.

In any event, the feed rate of the hydrocarbon feedstock will generally be between about 100 and about 1000 GHSV, and, preferably, between about 400 and about 500 GHSV. When air is, utilized as a source of free oxygen, a feed rate of about 200 to about 10,000 GHSV and preferably about 1200 to 1500 GHSV is utilized. The volumetric ratio of gaseous feed components, specifically ethane to free oxygen, will be between about 1/1 and about 30/1 and preferably about 1/1 and about 3/1. Inert gases such as nitrogen, helium and the like can be utilized as a diluent or a substitute for the nitrogen of air, when the free oxygen containing gas is oxygen or an oxygen-enriched air. Reaction temperatures may vary between about 600° C. and about 775° C., and are, preferably, between about 650° C. and 725° C. Total pressures may vary from about 0.5 to about 10 atmospheres and are preferably around 1 atmosphere.

The following examples are illustrative. All catalysts of the examples were prepared by adding 237.78 grams of $Na_2S.9H_2O$ and 25 cc's of deionized water to 215.4 grams of $CoCl_2.6H_2O$. The resulting percipitate was filtered and washed with deionized water and refiltered. To this filter cake was added $Na_4P_2O_7.10H_2O$ (15 grams), KOH (3 grams), $ZrO(NO_3)_2.nH_2O$(53.4 gram, and $NH_4Cl$(10.8 gram). Enough water was added to make a thick slurry which was dried overnight at about 150° C. The dried material was calcined for 3 hours at 1500° F. Contact materials A and B were calcined in a closed quartz vessel that provided for nitrogen flow through it and over the solid material. Contact materials C and D were calcined in an open dish with nitrogen flowing through the oven at 2SCF/hr.

All contact materials were ground and sieved to 20/40 mesh prior to evaluation.

The reactions were carried out by charging a 7 mm internal diameter quartz tube with 5 cc of contact material. The tube was placed in a furnace and a feed (150 cc/min. of air and 50 cc/min. of ethane) was passed over the contact material. The temperature of the furnace was usually about 650° C., except where indicated. Reactivation of the contact material was preformed by stopping the feed of ethane and air and substituting methylchloride or ethane as indicated. Product analysis was by standard gas chromatographic procedures. Conversion is mole percent of ethane converted and selectivity and yields are based on the mole percent of methane feed converted to a particular product.

TABLE 1

Contact Material A

| Sample | Time on stream | Conversion | Yield | Selectivity to $C_2^=$ |
|---|---|---|---|---|
| 1 | 3 min. | 87.7 | 67.7 | 77.1 |
| 2 | 36 min. | 76.9 | 65.3 | 84.9 |
| 3 | 1 hr. 10 min. | 80.0 | 70.4 | 88.1 |
| 4 | 2 hr. 8 min. | 55.9 | 52.6 | 94.2 |
| 5 | 4 hr. 9 min.* | 57.3 | 53.6 | 93.6 |
| 6 | 6 hr. 28 min.** | 73.8 | 63.4 | 89.6 |
| 7 | 7 hr. 27 min.** | 55.8 | 51.6 | 92.5 |
| 8 | 8 hr. 31 min.** | 31.3 | 30.2 | 96.3 |
| reactivate with 5% $CH_3Cl$ in $N_2$ - 1 hr. 33 min. at 650° C. | | | | |
| 9 | 3 min. | 61.7 | 52.4 | 85.0 |
| 10 | 32 min.* | 83.4 | 71.6 | 85.9 |
| 11 | 1 hr. 1 min.* | 79.5 | 69.3 | 87.2 |
| 12 | 2 hr. 56 min.* | 77.9 | 68.8 | 88.3 |
| 13 | 19 hr. 19 min.* | 47.8 | 43.4 | 90.8 |
| 14 | 20 hr. 21 min.* | 53.3 | 48.1 | 90.3 |
| 15 | 21 hr. 45 min.* | 57.3 | 51.2 | 89.3 |

*reactor furnace set to 665° C.
**reactor furnace set to 690° C.

TABLE 2

Contact Material B

| Sample | Time on stream | Conversion | Yield | Selectivity to $C_2^=$ |
|---|---|---|---|---|
| 1 | 4 min. | 52.8 | 41.2 | 78.1 |
| 2 | 38 min. | 90.5 | 77.0 | 85.1 |
| 3 | 1 hr. 20 min. | 69.1 | 62.0 | 89.7 |
| 4 | 1 hr. 59 min. | 83.2 | 74.5 | 89.6 |
| 5 | 2 hr. 33 min. | 79.7 | 72.8 | 91.4 |
| 6 | 3 hr. 7 min. | 53.6 | 51.0 | 95.0 |
| 7 | 3 hr. 51 min. | 50.5 | 48.2 | 95.4 |
| 8 | 18 hr. 42 min. | 56.1 | 52.5 | 93.6 |
| 9 | 20 hr. 5 min. | 41.5 | 39.2 | 94.5 |
| 10 | 21 hr. 13 min. | 47.8 | 45.2 | 94.5 |

TABLE 2-continued

Contact Material B

| Sample | Time on stream | Conversion | Yield | Selectivity to $C_2=$ |
|---|---|---|---|---|
| reactivation with ethane only - 2 hr. 39 min. | | | | |
| 11 | 3 min. | 24.6 | 17.1 | 69.4 |
| 12 | 37 min. | 44.5 | 41.4 | .93.1 |
| 13 | 1 hr. 11 min. | 55.4 | 50.5 | 91.2 |
| 14 | 1 hr. 51 min. | 65.6 | 58.2 | 88.8 |
| 15 | 2 hr. 27 min. | 36.5 | 34.5 | 94.4 |
| 16 | 3 hr. 4 min. | 42.5 | 39.9 | 94.0 |
| 17 | 19 hr. 22 min. | 34.8 | 32.6 | 93.6 |
| 18 | 20 hr. 12 min. | 35.0 | 32.9 | 93.8 |
| 19 | 20 hr. 47 min. | 24.7 | 23.5 | 94.9 |
| 20 | 21 hr. 21 min. | 25.7 | 24.3 | 94.6 |

TABLE 3

Contact Material C

| Sample | Time on stream | Conversion | Yield | Selectivity to $C_2=$ |
|---|---|---|---|---|
| 1 | 3 min. | 85.1 | 69.8 | 81.9 |
| 2 | 35 min. | 9.9 | 9.8 | 98.9 |
| reactivation with 10% $CH_3Cl$ in $N_2$ - 1 hr. at 650° C. | | | | |
| 3 | 3 min. | 67.7 | 60.0 | 88.7 |
| 4 | 36 min. | 15.1 | 15.0 | 99.5 |
| 5 | 125 min. | 2.3 | 2.3 | 100.0 |
| reactivation with 10% $CH_3Cl$ in $N_2$ - 1 hr. at 650° C. | | | | |
| 6 | 4 min. | 72.4 | 63.1 | 87.1 |
| 7 | 36 min. | 17.4 | 17.4 | 99.5 |
| reactivation with 10% $CH_3Cl$ in $N_2$ - 1 hr. at 650° C. | | | | |
| 8 | 3 min. | 72.6 | 62.5 | 86.1 |
| 9 | 38 min. | 19.3 | 19.17 | 99.3 |
| cool down overnight and reheat to 650° all under $N_2$ | | | | |
| 10 | 3 min. | 11.8 | 11.7 | 98.6 |
| reactivation with 10% $CH_3Cl$ in $N_2$ - 1 hr. 4 min. at 650° C. | | | | |
| 11 | 4 min. | 80.4 | 65.2 | 81.1 |
| 12 | 40 min. | 50.8 | 46.8 | 92.1 |
| 13 | 1 hr. 14 min. | 9.0 | 8.9 | 98.2 |
| 14 | 2 hr. 27 min. | 4.2 | 4.2 | 100.0 |
| reactivation with 10% $CH_3Cl$ in $N_2$ - 1 hr. at 650° C. | | | | |
| 15 | 3 min. | 40.2 | 28.7 | 71.4 |
| 16 | Bad sample, no data | | | |
| 17 | 1 hr. 11 min. | 76.4 | 66.9 | 87.6 |
| 18 | 1 hr. 44 min. | 77.1 | 67.2 | 87.2 |
| 19 | 2 hr. 15 min. | 73.5 | 65.5 | 89.1 |
| 20 | 17 hr. 15 min. | 39.0 | 36.8 | 94.4 |
| 21 | 22 hr. 47 min. | 29.8 | 28.8 | 96.8 |

TABLE 4

Contact Material D

| Sample | Time on stream | Conversion | Yield | Selectivity to $C_2=$ |
|---|---|---|---|---|
| 1 | 4 min. | 90.3 | 74.7 | 82.7 |
| 2 | 41 min. | 11.5 | 11.5 | 100. |
| reactivation with 10% $CH_3Cl$ in $N_2$-1 hr. at 650° followed by ethane - GHSV 600 - 1 hr. at 650° | | | | |
| 3 | 3 min. | 64.4 | 52.9 | 82.1 |
| 4 | 36 min. | 80.5 | 68.6 | 85.3 |
| 5 | 1 hr. 10 min. | 75.1 | 66.8 | 89.0 |
| 6 | 16 hr. 25 min. | 31.3 | 29.9 | 95.3 |
| 7 | 17 hr. 21 min. | 30.43 | 29.2 | 96.0 |
| 8 | 18 hr. 21 min. | 31.0 | 29.5 | 95.3 |
| 9 | 19 hr. 14 min. | 31.1 | 29.3 | 94.1 |

Several pertinent observations can be made from the data of the previous tables.

The contact material of Table 1 was initially an active material, having originally contained chlorine and been prepared in a $N_2$ atmosphere. However, its conversion deteriorated after a period of time. The chlorine treatments reactivated the contact material by raising the conversion of ethane to near the initial activity and sustaining the conversion for a longer period of time than that achieved by the fresh contact material.

As previously indicated, it appears that this contact material becomes "overoxidized" after a period of time. The contact material of Table 2 was the same "good" contact material as in Table 1, and treatment with ethane without $O_2$ present did raise the conversion to near the initial conversion. The effect was short lived and deterioration began again after about 2 hours. However, it should be noted that the reaction periods at high activity were found to be substantially longer than those in which ethane without $O_2$ is cycled with $O_2$ for reactivation.

The contact material of Table 3 (calcined under poor conditions of $O_2$ exclusion) resulted in poor initial activity. Treatment with chlorine in five stages raised the conversion and selectivity to acceptable levels and this activity was sustained for a long period of time after the final treatment. Again, the reaction periods between chlorine treatments were found to be substantially longer than conventional $C_2H_6/O_2/C_2H_6/O_2$ cycling.

The contact material of Table 4 was the same "poor" contact material used in Table 3. However, a single treatment with chlorine followed by ethane (without $O_2$ feed) raised the activity to that of a "good" contact material and sustained this activity for a long period of time.

The present invention is further illustrated by the following examples of the oxidative conversion of methane to ethylene, utilizing contact materials (1) and (4).

In addition to methane, the hydrocarbon feedstock, employed in the conversion of methane to ethylene, may contain other hydrocarbon or non-hydrocarbon components. The presence of ethane, propane and the like is not detrimental. It has been found that carbon dioxide and water are not detrimental, since they are often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent" is meant to include any gaseous or vaporous material present in the methane-containing gas, the free oxygen containing gas or in the form of an added gas or vapor, which is essentially inert with respect to the oxidative conversion of methane and, thus, does not significantly decrease the conversion of methane and/or the selectivity to the production of higher hydrocarbons. Such diluents can include, helium, nitrogen, steam, etc.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

It has been found that the method can be carried out between two extremes, namely, low conversion of methane/high selectivity to higher hydrocarbons, particularly ethylene, and high conversion of methane/low selectivity to the higher hydrocarbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane attainable, the contact materials are not readily poisoned and will tolerate the presence of water, carbon dioxide, carbon monoxide and the like. In addition, the contact materials appear to be long lived. Concomitantly, the process can be carried out continuously in fixed, moving, fluidized, ebullating or entrained bed reactors.

In these examples the contact materials were prepared by slurrying appropriate compounds of the components, drying in air and finally, calcining in air. The lithium oxide/magnesium oxide contact material was formed from lithium carbonate and magnesium oxide. The amounts utilized produce a contact material having an atomic ratio of lithium/magnesium of 1/6. The lithium oxide/titanium oxide contact material was prepared from lithium carbonate and titanium oxide and resulted in a lithium to titanium atomic ratio of 3/1.

5 cc of the contact materials were placed in a quartz tube, which in turn was placed in a furnace. Feed methane and air were passed through the body of contact material at a rate to produce a methane/free oxygen ratio of 10/1. Temperatures were maintained between about 730° C. and 740° C. and the gas hourly space velocity was about 1,000. Run 1 was conducted for a period sufficient to reach a steady state of conversion and selectivity. Thereafter, three incremental amounts of methylene chloride, totaling about 0.7 ml, were was added to the feed stream over a period of several minutes and, accordingly, was the equivalent of a single slug of the chlorine-containing material. The results listed as Run 2 were taken approximately 24 hours after the chlorine treatment. Run 3 was likewise conducted for a period sufficient to attain essentially constant conversion and selectivity. Thereafter, five increments of methylene chloride were added at one hour intervals, thus resulting in 0.5 ml of methylene chloride being added over a 5 hour period. Run 4 lists the results of sampling after the addition of the chlorine was completed.

TABLE 5

| Run No. | Contact Material | Chlorinated | % Conversion of $CH_4$ | Selectivity To $C_2^=$ | To $C_2$ | To CO + $CO_2$ |
|---|---|---|---|---|---|---|
| 1 | $Li_2O/MgO$ | No | 10.0 | 31 | 42 | 18 |
| 2 | $Li_2O/MgO$ | Yes | 9.9 | 43 | 31 | 14 |
| 3 | $Li_2O/TiO_2$ | No | 9.3 | 37 | 38 | 19 |
| 4 | $Li_2O/TiO_2$ | Yes | 14.1 | 48 | 21 | 16 |

It has also been found that the production of $CO_2$ was high and, hence, the HC selectivity was low, if the concentration of $O_2$ in the initial feed stream is high. Accordingly, the HC selectivity can be increased and the $CO_2$ production concomitantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

That which is claimed:

1. A method for the oxidative conversion of methane to higher hydrocarbons, comprising the steps of:
   (a) contacting a feed material comprising methane and a free oxygen-containing gas with a solid contact material selected from the group consisting of:
      (i) a solid contact material consisting essentially of: (A) cobalt, (B) at least one metal selected from the group consisting of zirconium, zinc and niobium, (C) phosphorous, (D) oxygen and (E) at least one of halogen ions and compounds containing halogen ions; and
      (ii) a solid contact material consisting essentially of: (A) cobalt, (B) at least one metal selected from the group consisting of zirconium, zinc and niobium, (C) phosphorous, (D) oxygen, (E) at least one material selected from the group consisting of Group IA metals, sulfur, compounds containing sulfur and mixtures thereof and (F) at least one of halogen ions and compounds containing halogen ions;
   under oxidative conversion conditions sufficient to convert said methane to said higher hydrocarbons; and
   (b) at least intervally contacting said solid contact material with at least one material containing at least one halogen and with at least one material containing at least one reducing agent in the absence of said free oxygen-containing gas.

2. A method in accordance with claim 1, wherein the introduction of the free oxygen-containing gas is intervally discontinued, and the material containing at least one reducing agent is substituted therefor.

3. A method in accordance with claim 2, wherein the material containing at least one reducing agent thus substituted for the free oxygen-containing gas is methane.

4. A method in accordance with claim 1, wherein the introduction of the feed material and the free oxygen-containing gas is intervally discontinued, and the material containing at least one reducing agent is substituted for the free oxygen-containing gas.

5. A method in accordance with claim 4, wherein the material containing at least one halogen is intervally contacted with the contact material simultaneously with the material containing at least one reducing agent.

6. A method in accordance with claim 4, wherein the material containing at least one halogen is intervally contacted with the contact material prior to thus substituting the material containing at least one reducing agent for the free oxygen-containing gas.

7. A method in accordance with claim 6, wherein the introduction of the methane is resumed after thus contacting the contact material with the material containing at least one halogen and the material containing at least one reducing agent thus substituted for the free oxygen-containing gas is said methane.

8. A method for the oxidative dehydrogenation of feed organic compounds, consisting essentially of saturated $C_2$ to $C_7$ hydrocarbons, to product organic compounds, comprising less saturated hydrocarbons, comprising the steps of:

(a) contacting said feed organic compounds and a free oxygen containing gas with a solid contact material selected from the group consisting of:

(1) a solid contact material, consisting essentially of: (A) at least one metal selected from the group consisting of Group IA metals, Group IIA metals and mixtures thereof, (B) oxygen, and (C) at least one of halogen ions and compounds containing halogen ions;

(2) a solid contact material, comprising: (A) at least one metal selected from the group consisting of Group IA metals, (B) at least one metal selected from the group consisting of Lanthanum Series metals, (C) oxygen and (D) at least one of halogen ions and compounds containing halogen ions;

(3) a solid contact material, comprising: (A) at least one metal selected from the group consisting of Group IA metals, (B) at least one metal selected from the group consisting of Group IIA metals, (C) at least one metal selected from the group consisting of Lanthanum Series metals, (D) oxygen and (E) at least one of the halogen ions and compounds containing halogen ions;

(4) a solid contact material, consisting essentially of: (A) at least one metal selected from the group consisting of Group IA metals, (B) zinc, (C) oxygen and (D) at least one of halogen ions and compounds containing halogen ions;

(5) a solid contact material, consisting essentially of: (A) at least one metal selected from the group consisting of Group IA metals, (B) at least one metal selected from the group consisting of Group IIA metals, (C) zinc, (D) oxygen and (E) at least one of halogen ions and compounds containing halogen ions;

(6) a solid contact material, consisting essentially of: (A) at least one metal selected from the group consisting of Group IA metals, (B) at least one metal selected from the group consisting of titanium and zirconium, (C) oxygen and (D) at least one of halogen ions and compounds containing halogen ions;

(7) a solid contact material, consisting essentially of: (A) at least one metal selected from the group consisting of Group IA metals, (B) at least one metal selected from the group consisting of Group IIA metals, (C) at least one metal selected from the group consisting of titanium and zirconium, (D) oxygen and (E) at least one of halogen ions and compounds containing halogen ions;

(8) a solid contact material, consisting essentially of: (A) at least one metal selected from the group consisting of Group IA metals, Group IIA metals and mixtures thereof, (B) at least one of phosphate radicals and compounds containing phosphate radicals and (C) at least one of halogen ions and compounds containing halogen ions;

(9) a solid contact material, comprising: (A) cobalt, (B) at least one metal selected from the group consisting of zirconium, zinc, niobium, indium, lead and bismuth, (C) phosphorous, (D) oxygen and (E) at least one of halogen ions and compounds containing halogen ions; and

(10) a solid contact material, comprising: (A) cobalt, (B) at least one metal selected from the group consisting of zirconium, zinc, niobium, indium, lead and bismuth, (C) phosphorous, (D) oxygen, (E) at least one of halogen ions and compounds containing halogen ions and (F) at least one material selected from the group consisting of Group IA metals, sulfur, compounds containing sulfur and mixtures thereof;

under conditions sufficient to convert said feed organic compounds to said product organic compounds; and (b) at least intervally contacting said solid contact material with a material containing at least one halogen, when said solid contact material is selected from the group consisting of contact materials (1), (2), (3), (4), (5), (6), (7) and (8), and with at least one material containing at least one halogen and with at least one material containing at least one reducing agent in the absence of said free oxygen containing gas, when said solid contact material is selected from the group consisting of contact materials (9) and (10).

9. A method in accordance with claim 8, wherein the solid contact material is a contact material selected from the group consisting of (9) and (10), and the introduction of the free oxygen-containing gas is intervally discontinued and a material containing at least one reducing agent is substituted therefor.

10. A method in accordance with claim 9, wherein the feed organic compounds comprise ethane, and the material containing at least one reducing agent thus substituted for the free oxygen containing gas is said ethane.

11. A method in accordance with claim 8, wherein an ineffective amount of halogen is initially present in the contact material, and said amount of halogen is increased to at least an effective amount of contacting said contact material with the material containing at least one halogen prior to contacting the feed organic compounds and the free oxygen containing gas with said contact material.

12. A method in accordance with claim 11, wherein the contact material is thus contacted with the material containing at least one halogen, prior to contacting the feed organic compounds and the free oxygen containing gas with said contact material, in a reaction zone in which the oxidative dehydrogenation is carried out.

13. A method in accordance with claim 11, wherein the contact material is also intervally contacted with the material containing at least one halogen during the conduct of the oxidative dehydrogenation.

14. A method in accordance with claim 11, wherein the contact material is also contacted with the material containing at least one halogen by continuously adding said material containing at least one halogen to the feed organic compounds and the free oxygen containing gas during the conduct of the oxidative dehydrogenation.

15. A method in accordance with claim 8, wherein an effective amount of halogen is initially present in the contact material, and the contact material is intervally contacted with the material containing at least one halogen during the conduct of the oxidative dehydrogenation.

16. A method in accordance with claim 8, wherein an effective amount of halogen is initially present in the contact material, and the contact material is continuously contacted with the material containing at least one halogen during the conduct of the oxidative dehydrogenation.

17. A method in accordance with claim 8, wherein the solid contact material is contact material (6), the introduction of the feed organic compound and the free oxygen containing gas is intervally discontinued, and the material containing at least one reducing agent is substituted for said free oxygen containing gas.

18. A method in accordance with claim 17, wherein the material containing at least one halogen is intervally contacted with the contact material simultaneously with the material containing at least one reducing agent.

19. A method in accordance with claim 17, wherein the material containing at least one halogen is intervally contacted with the contact material prior to thus substituting the material containing at least one reducing agent for the free oxygen containing gas.

20. A method in accordance with claim 19, wherein the feed organic compounds comprise ethane, the introduction of said ethane is resumed after thus contacting the contact material with the material containing at least one halogen, and the material containing at least one reducing agent thus substituted for the free oxygen containing gas is said ethane.

* * * * *